(12) United States Patent
Ducce

(10) Patent No.: US 11,883,582 B2
(45) Date of Patent: Jan. 30, 2024

(54) INHALER

(71) Applicant: ASTRAZENECA AB, Sodertalje (SE)

(72) Inventor: Rune Ducce, Sodertalje (SE)

(73) Assignee: ASTRAZENECA AB, Sodertalje (SE)

( * ) Notice: Subject to any disclaimer, the term of this patent is extended or adjusted under 35 U.S.C. 154(b) by 524 days.

(21) Appl. No.: 17/071,499

(22) Filed: Oct. 15, 2020

(65) Prior Publication Data
US 2021/0196908 A1 Jul. 1, 2021

Related U.S. Application Data

(60) Provisional application No. 62/916,412, filed on Oct. 17, 2019.

(51) Int. Cl.
*A61M 15/00* (2006.01)

(52) U.S. Cl.
CPC ........ *A61M 15/007* (2014.02); *A61M 15/009* (2013.01); *A61M 15/0081* (2014.02); *A61M 15/0091* (2013.01); *A61M 15/0026* (2014.02)

(58) Field of Classification Search
CPC ............ A61M 15/007; A61M 15/0081; A61M 15/009; A61M 15/0091; A61M 15/0026
See application file for complete search history.

(56) References Cited

U.S. PATENT DOCUMENTS

| | | | | |
|---|---|---|---|---|
| 5,027,808 A * | 7/1991 | Rich | ................ | A61M 15/0091 128/200.23 |
| 5,347,998 A * | 9/1994 | Hodson | ............ | A61M 15/0095 128/200.23 |
| 6,439,227 B1 * | 8/2002 | Myrman | ........... | A61M 15/0091 128/200.14 |
| 8,225,790 B2 * | 7/2012 | Bowman | ........... | A61M 15/0091 239/338 |
| 8,578,932 B2 * | 11/2013 | Andersen | .......... | A61M 15/0091 128/200.14 |
| 11,083,855 B2 * | 8/2021 | Richardson | ......... | A61M 15/009 |
| 2003/0116155 A1 * | 6/2003 | Rasmussen | ....... | A61M 15/0091 128/200.23 |
| 2003/0136401 A1 * | 7/2003 | Jansen | .............. | A61M 15/0091 128/200.23 |
| 2003/0183225 A1 * | 10/2003 | Knudsen | ............. | A61M 15/008 128/200.23 |

(Continued)

FOREIGN PATENT DOCUMENTS

| | | |
|---|---|---|
| EP | 0414536 A2 | 2/1991 |
| EP | 0490797 A1 | 6/1992 |

(Continued)

*Primary Examiner* — Tu A Vo

(57) ABSTRACT

An inhaler 10 for delivery of a medicament by inhalation. The inhaler 10 has a drive mechanism, a canister drive 22 for receiving a canister 50 of medicament, a spring 20, and a trigger mechanism with a latch 35. The latch 35 has a locked position to prevent linear movement of the canister drive 22 and holds the spring 20 in a loaded configuration; and an unlocked position in which the latch 35 is disengaged from the canister drive 22. The trigger mechanism comprises a blocker 32. The blocker 32 has a blocking position in which it contacts the latch 35 to block movement from the locked position to the unlocked position; and a rotated position in which the blocker 32 is disengaged from the latch 35 to allow it to lock and unlock.

13 Claims, 10 Drawing Sheets

(56) References Cited

U.S. PATENT DOCUMENTS

| | | | | |
|---|---|---|---|---|
| 2004/0020486 A1* | 2/2004 | Huxham | ............ | A61M 15/009 |
| | | | | 128/200.23 |
| 2004/0107962 A1* | 6/2004 | Harrison | ........... | A61M 15/0096 |
| | | | | 128/200.23 |
| 2006/0243275 A1* | 11/2006 | Ruckdeschel | ..... | A61M 15/0091 |
| | | | | 128/200.23 |
| 2007/0102455 A1* | 5/2007 | Stark | ................... | B05B 11/1032 |
| | | | | 222/207 |
| 2008/0178872 A1* | 7/2008 | Genova | ............ | A61M 15/0065 |
| | | | | 128/200.23 |
| 2008/0289629 A1* | 11/2008 | Djupesland | ....... | A61M 15/0086 |
| | | | | 128/203.15 |
| 2010/0313884 A1* | 12/2010 | Elliman | .................. | G06M 1/04 |
| | | | | 128/203.12 |
| 2015/0020798 A1* | 1/2015 | Elgaard | ............ | A61M 15/0025 |
| | | | | 128/200.23 |
| 2015/0101599 A1* | 4/2015 | Berry | ................ | A61M 15/0025 |
| | | | | 128/202.22 |

FOREIGN PATENT DOCUMENTS

| | | | | |
|---|---|---|---|---|
| EP | 2755707 A1 | 7/2014 | | |
| EP | 3345644 A1 * | 7/2018 | ............ | A61M 15/00 |
| EP | 3345644 A1 | 7/2018 | | |
| WO | 2004028608 A1 | 4/2004 | | |
| WO | WO-2017176693 A1 * | 10/2017 | .......... | A61M 15/002 |
| WO | 2019170718 A1 | 9/2019 | | |
| WO | WO-2019170718 A1 * | 9/2019 | ........ | A61M 15/0013 |

\* cited by examiner

FIG. 4
FIG. 5
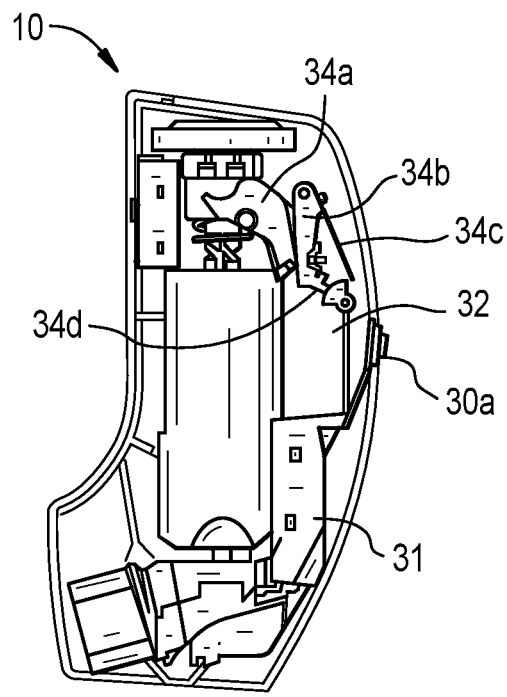
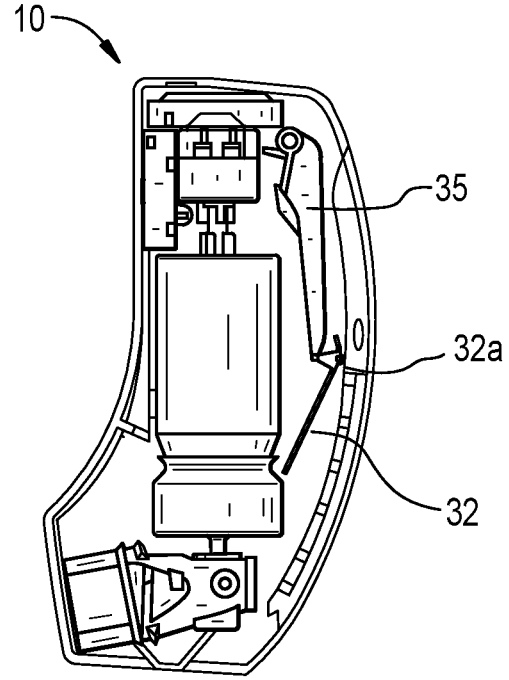

INHALER

This application claims benefit under 35 U.S.C. § 119(e) of the following U.S. Provisional Application No. 62/916,412 filed Oct. 17, 2019. The above listed application is incorporated by reference herein in its entirety for all purposes.

TECHNICAL FIELD

The present invention relates to an inhaler for delivery of a medicament by inhalation and methods of operation thereof, and in particular to the mechanisms of the inhaler for dispensing a dose of medicament and to the components for triggering dispensing of a dose and for controlling dispensing of a dose. The present invention also relates to a method of dispensing medicament from an inhaler, and in particular to a method of dispensing a dose of medicament from the inhaler.

BACKGROUND OF THE INVENTION

There are many ways to provide a dose of medicament to a patient or other intended recipient of the medicament, particularly when it is desired to provide multiple doses of the medicament, for example as part of a treatment regimen or otherwise. Many medicaments, such as those for treating pulmonary or other conditions, are delivered/dispensed to the recipient by inhalation using a suitable inhaler. One commonly used and effective type of multiple dose inhaler is a pressurised metered dose inhaler (pMDI) in which a canister containing medicament in the inhaler is actuated, e.g. by compression, to deliver/dispense a metered dose of the medicament through a mouthpiece to a user. A particularly user-friendly type of such inhaler is configured to deliver/dispense a dose of medicament automatically, having an actuation mechanism to actuate the canister when a triggered. The actuation mechanism is typically breath-actuated, i.e. triggered by inhalation of a user through a mouthpiece. This ensures that a dose of medicament is dispensed whilst the user is inhaling, which is particularly advantageous since dispensing of a dose of medicament is co-ordinated with inhalation of the dose and synchronisation of the patient's breath-intake (or inspiration) ensures optimal delivery of aerosol medication to the target region in the respiratory tract, with minimal losses due to deposition in the mouth and pharynx. For multiple dose inhalers, the triggering and dispensing mechanisms must be reset after each actuation to enable a subsequent dose to be dispensed when required.

An example breath-actuated pMDI is described in WO-A-2013/038170. The actuation mechanism of this inhaler is operable to compress a canister containing medicament to deliver a metered dose of the medicament in response to inhalation by a user. The actuation mechanism comprises a spring to compress the canister and a trigger mechanism to prevent the spring compressing the canister until a dose is to be dispensed. When a user inhales through a mouthpiece, the trigger mechanism releases the spring, which then compresses the canister to deliver a dose of medicament through a valve of the canister and into the mouthpiece. A resetting mechanism interacts with a rotating cover or cap for the mouthpiece such that movement of the cover into a closed position resets the spring.

Whilst the inhaler disclosed in this application is effective and reliable at dispensing multiple, consecutive doses to a user, the trigger mechanism of this arrangement comprises several components that require numerous manufacture and assembly steps and that have fairly tight tolerances, and some components are made of very different materials that must be affixed, e.g. welded, together. Therefore, it is possible that the trigger mechanism of the prior art inhaler may be less robust and more sensitive to manufacturing tolerances than is desirable and the reliability of the inhaler may be impacted as a result.

Therefore, there remains a need for an inhaler for delivery of a medicament by inhalation, and a method of dispensing a medicament from an inhaler, with improved reliability and consistency throughout the lifetime of the inhaler and across manufactured batches of the inhaler.

SUMMARY OF THE INVENTION

In accordance with the present invention, from a first broad aspect, there is provided an inhaler for delivery of a medicament by inhalation, the inhaler comprising: a drive mechanism comprising a canister drive for receiving a canister of medicament, a biasing means, and a trigger mechanism; wherein: the trigger mechanism comprises: a latch having: a locked position in which it contacts the canister drive to prevent linear movement of the canister drive and holds the biasing means in a loaded configuration; and an unlocked position in which the latch is disengaged from the canister drive and releases the biasing means from the loaded configuration to drive the canister drive from a rest position to an actuated position; and a blocker having: a blocking position in which it contacts the latch to block movement thereof from the locked position to the unlocked position; and a rotated position in which the blocker is disengaged from the latch and allows movement of the latch from the locked position to the unlocked position; and the blocker is rotatable in response to a force applied to the blocker.

The claimed inhaler overcomes at least one of the drawbacks of the prior art. For example, an inhaler is provided in which a reduced number of components, compared with the prior art, form a trigger mechanism that reliably releases a canister drive for movement under a force from a loaded biasing means, to dispense a dose of medicament from a canister received within the canister drive. Having fewer components performing this function compared with the prior art not only improves manufacturing ease, time and costs, but also may be more reliable and robust than prior art arrangements, as there are fewer parts that might fail and/or be misassembled and tolerances are improved. Having the latch engage with the canister drive and with the blocker provides a simple mechanism with only two components forming the trigger mechanism in this arrangement, compared with the multiple components disclosed in the prior art, for example in WO 2013/038170, and optionally the components can be formed from relatively rigid and robust materials (e.g. moulded plastic), whereas the more complex trigger mechanisms of the prior art require multiple components made from many different materials, including one component comprising two very different materials (metal and plastic) that requires separate assembly before use.

Furthermore, having a trigger mechanism comprising a reduced number of components also enables the components to be placed in different positions compared with the many components of the prior art mechanisms. For example, the blocker may be the lowermost component of the trigger mechanism when the inhaler is held generally in its in-use position (e.g. with the canister generally aligned with the valve beneath the canister body). In such a configuration, the blocker may be closer to a mouthpiece of the inhaler and thus the flow path between the mouthpiece and the blocker is shorter than the prior art arrangements. This may be particularly advantageous in arrangements in which the blocker comprises a flap, and the flap is rotatable in response to a pressure drop within the inhaler. Having a shorter flow path may provide a more reliable trigger mechanism.

In addition to, or as an alternative to the blocker comprising a flap, the inhaler may comprise a button for moving the blocker from the blocking position to the rotated position. The button may comprise any suitable means that is activatable by the user, for example manually activatable by pressure from a finger or the like, and that interacts with the blocker and/or with the latch when activated (e.g. pushed or pressed) to move the blocker into the rotated position. In some arrangements, the button is formed within or by another component of the inhaler. For example, the inhaler may further comprise an outer housing for encasing the drive mechanism, wherein the button comprises a protrusion through, or a deflectable portion of, the outer housing. In some arrangements, the button is a deflectable portion of the outer housing that is formed by co-moulding a more deformable material with a more rigid material forming the remainder of the outer housing. Thus a robust outer housing is provided but that has a portion that is easily deflectable by a user, e.g. manually deflectable, to activate the trigger mechanism and to dispense a dose from the inhaler. In the arrangement where the blocker comprises a flap, the button may comprise a protrusion that protrudes, for example, from the inner surface of the outer housing that is manually deflectable to come into contact with the latch and/or with the flap to push the flap into the rotated position to disengage from the latch. Where the button is formed by a material co-moulded with the outer housing, this may be advantageous compared with prior art button mechanisms since ingress of dust or dirt into the inhaler through any gap in the prior art arrangements is prevented by the co-moulded portions of the housing and a co-moulded outer housing and button arrangement may be simpler to assemble than the prior art button arrangements that require multiple separate components.

The blocker may return from the rotated position to the blocking position by any suitable means. For example, the blocker may return to the blocking position once the force is removed, such as by the effect of gravity. In some arrangements, the blocker is biased into the blocking position to ensure the blocker returns to this position to reset the trigger mechanism. For example, in some arrangements the trigger mechanism may further comprise a blocker spring for biasing the blocker into the blocking position. The blocker spring may be a separate component assembled within the inhaler in any appropriate manner, or may be formed as part of an existing component of the inhaler. For example, a separate spring abutting the blocker may be provided in a suitable location in the inhaler. In some arrangements, the inhaler further comprises a chassis for at least partially receiving at least one or more of the canister drive, the biasing means, the latch and the blocker, and the chassis may comprise a blocker spring or other biasing means and preferably it is integrally formed with the chassis. Such an arrangement is simple to manufacture and robust, as well as being easier to assemble than having separate components. In some arrangements, the biasing means comprises an elongate protrusion with one end affixed to the chassis and the other end free from the chassis to enable flexing of the free end of the blocker spring, the free end configured for abutting a portion of the blocker and biasing the blocker into the blocking position. Having an elongate and flexible protrusion or finger integrally formed with the chassis is thought to be particularly advantageous because the length of the protrusion or finger can be configured to provide the required amount of biasing to retain the blocker in the blocking position unless sufficient force is applied to the blocker (e.g. by manual activation of a button or due to a pressure drop under inhalation by a user) to overcome the biasing of the protrusion or finger to rotate the blocker into the rotated position. Once the force is removed or reduced, the protrusion or finger biases the blocker back to the blocking position to reset the trigger mechanism, at least in this respect. Therefore, a robust and reliable mechanism for resetting the blocker is provided in such arrangements.

As discussed above, the latch is configured to contact the canister drive in a locked position and disengage from the canister drive in an unlocked position. This can be achieved in any suitable manner. In some arrangements, the latch is rotatable between the locked position and the unlocked position. In some arrangements, the latch comprises a shelf configured for abutment with a ledge of the canister drive, the ledge protruding from the canister drive and biased to rest on the shelf under the load of the biasing means when the latch is in the locked position and further wherein rotation of the latch to the unlocked position tilts the shelf and the ledge disengages from the shelf to release the canister drive. Such an arrangement is thought to be particularly robust and will hold the canister drive against movement under the load of the biasing means reliably, as the ledge of the canister drive is pushed downwardly (when the inhaler is in its generally upright, in-use position) onto the top of the shelf. Only when the latch rotates to its unlocked position does the shelf move away from underneath the ledge and allows the canister drive to move downwardly as the biasing means releases its load.

When the canister drive is driven by the biasing means from the rest position to the actuated position, a canister received in the canister drive is also driven from its rest position to its actuated position by the movement of the canister drive to release a dose of medicament from the valve of the canister, as is known in the art. Whilst the canister drive may generally drive and guide the canister, it is possible that the canister may not be completely aligned as desired on each and every actuation. For example, and particularly as the load of the biasing means is generally quite large, it is possible that the canister may tilt during travel to its actuated position (i.e. during the downstroke), and this may affect compression of the canister relative to the stem of the canister valve, and/or the time it takes for the valve to reset time, both of which would be disadvantageous because it may affect dosing levels of the medicament. Therefore, in some arrangements, the inhaler further comprises at least one alignment guide for controlling the positioning of a canister received in the canister drive, such as when the canister is driven by the canister drive to the actuated position and/or when the canister returns to the rest position. By guiding the canister during motion, better alignment of the canister is ensured and more reliable dosing and/or reset may be achieved.

In some arrangements, the at least one alignment guide comprises an integrally formed portion of the canister drive. This arrangement is thought to be particularly advantageous as the canister drive drives the canister as well as ensuring its alignment when driven. For example, the alignment guide or guides may at least partially encircle a canister received in the canister drive, preferably having a close or fit with the canister to guide or support the canister within the canister drive. The alignment guide(s) can be integrally formed with the canister drive, e.g. can be a moulded part of the canister drive. Where there is a plurality of alignment guides, each guide may at least partially encircle a portion of a canister received in the canister drive, the alignment guides substantially forming at least a partial circumferential ring around the canister. It is thought that such an arrangement is particularly advantageous because the canister can be held in alignment without significantly adding to the weight of the device as the alignment guides can be fairly small and are arranged to grip or hug the canister as it moves in either direction.

The alignment guides are thought to be advantageous in their own right. Therefore from a further broad aspect of the present invention, there is provided an inhaler for delivery of a medicament by inhalation, the inhaler comprising a drive mechanism comprising a canister drive for receiving a canister of medicament and at least one alignment guide for controlling the positioning of a canister received in the canister drive, such as when the canister is driven by the canister drive to the actuated position and/or when the canister returns to the rest position.

As discussed above, the trigger mechanism is configured to release the canister drive to drive the canister guide and any canister contained therein to the actuated position to dispense a dose of medicament. For a multi-dose inhaler, it is necessary to reset the trigger mechanism ready to dispense the next dose. Therefore, in some arrangements the inhaler further comprises a resetting mechanism for resetting the drive mechanism, the resetting mechanism configured for moving the canister drive back to the rest position to reload the biasing means and to reset the trigger mechanism to the locked position. For example, the trigger mechanism may be moved and/or biased back to its latch locked and blocker blocking positions by the resetting mechanism. In some arrangements, the resetting mechanism comprises a rotatable cover configured to drive the canister drive back to the rest position under rotation of the cover, wherein movement of the canister drive towards the rest position may bring the ledge of the canister drive into engagement with a resetting protrusion on the latch to move the latch back into the locked position. This arrangement is thought to be particularly advantageous because it is a simple mechanism for the user to operate and would naturally do so as the cap closing will cover any mouthpiece of the inhaler, and having a resetting protrusion pushes the latch back into position whilst the blocker return spring biases the blocker back to its blocking position.

For multi-dose inhalers as discussed in some of the arrangements above, it can be advantageous to have one or more further mechanisms to improve usage and reliability of the inhaler. Therefore in some arrangements, the inhaler further comprises a return mechanism for returning a canister received in the canister drive from the actuated or fired position to the rest or ready-to-fire position, the return mechanism comprising a damping system, the damping system configured to enable the canister to automatically return from the fired position to the ready-to-fire position within a predetermined time period measured from the release of the biasing means from the loaded configuration. In these arrangements, the inhaler automatically returns the canister from the actuating position to the rest position, within a predetermined time period, such that the canister valve is returned to its refill point and refilled for a subsequent dose all within this time, irrespective of whether the user of the inhaler activates the resetting mechanism to restore the inhaler to its pre-fire configuration. This occurs over a period of time sufficient for the valve to dispense the entire current dose as the damping mechanism is configured to prevent the canister return occurring too quickly. Namely the valve is held open for a sufficient time to dispense the dose and the valve is returned at a suitable speed to allow the valve to refill completely, but the valve is not held in an open configuration for any longer than is necessary to perform these actions reliably. Furthermore, the valve is reset to its closed position sufficiently quickly that the user will still be holding the inhaler in an upright position, so the valve will be located beneath the canister. In these arrangements, at least a portion of the damping system such as a rod may interact with the canister drive and with the canister, and release of the canister drive concurrently drives the rod and it is the rod that pushes the canister from the ready-to-fire to the fired position.

Whilst the canister reset could be performed as a single step at one speed for the entire time period, optionally the damping system is configured such that the predetermined time period comprises a first time segment and a second time segment, wherein movement of the canister from the actuating position to the rest position is slower during the first time segment than during the second time segment. This arrangement optimises the time during which the valve is held open below its fire point (hereinafter referred to as Time Below Fire (TBF)) and so dispenses the entire dose effectively, but also minimises the time before the canister valve reaches its refill point (hereinafter referred to as Time To Refill (TTR)). As discussed above, all this occurs without the user needing to take any action as it is automatic and controlled by the damping mechanism. In some embodiments, during the first time segment the canister is maintained in the actuating position (i.e. there is no movement) and during the second time segment the canister returns from the actuating position to the rest position.

Whilst the predetermined time period might include other time segments, optionally the damping system is configured such that the second time segment immediately follows the first time segment, so the canister movement transitions immediately from slow return or substantially no movement to fast or faster return without any pause or delay inbetween.

Canisters for use in inhalers according to embodiments of the present invention have generally consistent profiles and configurations but differences between canisters due to tolerances should be expected and also the same canister may perform differently under different conditions. Other issues may be encountered towards the end of life (EOL) of the canister compared with the beginning of life (BOL), such as variability in the return force, which may degrade over time. Therefore, the damping system is optionally configured such that the tolerances and variations in performance are accounted for in inhalers of embodiments of the present invention. Optionally the first time segment is in the range of about 0.05 to 2.00 seconds, optionally in the range of about 0.10 to 1.75 seconds, optionally in the range of about 0.20 to 1.50 seconds, optionally in the range of about 0.30 to 1.25 seconds, optionally in the range of about 0.40 to 1.20 seconds. Time segments within one or more of these ranges have been found to be suitable at accounting for variations in performance and also at accounting for tolerances and differences between canisters and batches of canisters etc. Optionally the first time segment is at least about 0.20 seconds, optionally at least about 0.30 seconds, optionally at least about 0.40 seconds. These minimum times have been found to be optimal for ensuring the entire dose in the valve is dispensed each actuation.

Optionally the second time segment is in the range of about 0.10 to 2.00 seconds, optionally in the range of about 0.30 to 1.80 seconds, optionally in the range of about 0.40 to 1.70 seconds, optionally in the range of about 0.60 to 1.60 seconds, optionally in the range of about 0.80 to 1.50 seconds, optionally in the range of about 1.00 to 1.40 seconds. Again, time segments within one or more of these ranges have been found to be suitable at accounting for variations in performance and also at accounting for tolerances and differences between canisters and batches of canisters etc. Optionally the second time segment is less than about 2.0 seconds, optionally less than about 1.75 seconds, optionally less than about 1.50 seconds, optionally less than about 1.25 seconds, optionally about 1.20 seconds. These maximum times have been found to be optimal for ensuring the valve refills quickly and fully. As discussed above, it is thought to be particularly advantageous for the valve to be refilled fully whist the canister is held in a generally upright position, i.e. within a time frame of use by the user where the inhaler has not yet been removed from the user's mouth. Optionally the first time segment combined with the second time segment is a total time of less than about 2.5 seconds, optionally less than about 2.00 seconds, optionally less than about 1.75 seconds, optionally less than about 1.50 seconds. This provides a sufficient time for the valve to dispense and refill but is not so long as to adversely affect the quality of valve refill or to allow the user to significantly reposition the inhaler from the upright position in which it is used.

As discussed above, the inhaler comprises a damping system to provide the damped movement during the predetermined time period. Optionally the damping system comprises a rotary damper. Such dampers are available and perform reliably over multiple uses and are suited for use in embodiments of the present invention. Examples of such devices are rotary dampers as sold by ACE Controls International/Inc. or ACE Stoßdämpfer GmbH, etc.

Optionally the damping system comprises a rod, the rod coupled with a shaft of the rotary damper such that the rod rotates with the shaft, the rod rotation being controlled by the shaft rotation in at least a first direction of rotation. Thus, movement of the rod is controlled by the damper. Optionally the rod is moveable relative to the shaft in an axial direction. Optionally the moving component comprises a cam follower and the rod comprises a cam track for receiving the cam follower, the cam track and the cam follower being configured such that the cam follower abuts an edge of the cam track and applies an axial moving force to the rod when the moving component moves from the first position to the second position. Thus, a mechanical arrangement is provided in which the rod can move rotationally and/or axially in at least one and optionally two directions. Optionally the cam track and the cam follower are configured such that the axial moving force applied by the cam follower to the edge of the cam track axially moves the rod in a direction away from the shaft and the rod thereby applies a driving force to the canister to drive the canister from the rest position to at least the actuating position. Optionally the cam track comprises at least a first section and a second section, the first section being substantially aligned with the axis of the rod and the second section being curved about a portion of the outer surface of the rod in a direction substantially away from the first section of the track. Thus, the two speeds of movement of the rod are provided. The first section of track is configured to allow axial movement of the rod relative to the cam follower and the second section of the track is configured to allow axial and rotational movement of the rod relative to the cam follower. Rotational movement of the rod is damped by the rotational damper and the axial movement of the rod is not damped by the rotational damper so, for example, the combined rotational and axial movement of the rod is controlled and slower and when the cam follower reaches the axial section of the track, more rapid movement of the rod in the axial direction is enabled. Optionally the second section of the track is substantially helical about the portion of the outer surface of the rod. This provides a smooth and controlled movement of the cam follower. Optionally, for balance and improved control, the rod comprises a pair of cam tracks diametrically opposed on the rod outer surface, optionally wherein the second sections of the cam tracks are helical and the helices are either both right-handed or both left-handed.

As discussed above, optionally the cam track is configured such that a first section of the cam track is configured such that the damping system enables the canister to automatically return from the actuating position to the rest position initially at a first speed and is further configured such that the damping system enables the canister to automatically return from the actuating position to the rest position at a second speed at a later time within the predetermined time period. This enables efficient dose dispensing and refill of the canister valve within an appropriate time. In alternative embodiments, as the yoke has not reached its stop position abutting the portions of the cap when the canister has reached its actuating position, the cam track is configured such that the damping system enables the yoke to continue to move and the canister is maintained in its actuating position during yoke movement, and the cam track is further configured such that the damping system enables the canister to automatically return from the actuating position to the rest position at a later time within the predetermined time period, after the yoke movement has ceased. This enables efficient dose dispensing and refill of the canister valve within an appropriate time, Prior to activation of the inhaler, the inhaler may be held in a closed configuration for many hours and may only be used once or twice a day, for example. Therefore, it is helpful in some embodiments to relieve the loading of the biasing means to reduce or avoid stresses on certain components of the inhaler. Optionally the inhaler further comprises a load-relieving mechanism configured to support at least one of the moving component and at least a part of the damping system in a spaced apart position in which the moving component and/or the part of the damping system is not in contact with the canister, when the canister is received in the inhaler body. Thus, the stresses that might otherwise be imparted by the loaded biasing means to components of the inhaler are reduced or otherwise alleviated. Optionally the load-relieving mechanism is configured to release the moving component and/or the part of the damping system to thereby bring the moving component and/or the part of the damping system, under the load of the biasing means, into contact with the canister, when the canister is received in the inhaler body. This may be directly or indirectly via another component or mechanism of the inhaler.

Optionally the load-relieving mechanism is configured to release the moving component to thereby bring the rod of the damping system, under the load of the biasing means, into contact with the canister, when the canister is received in the inhaler body, such that the rod is enabled to apply the driving force to the canister to drive the canister from the rest position to at least the actuating position. Thus, the rod only contacts the canister when the biasing force is about to be applied to the canister and reduces the likelihood of wear of the rod when the inhaler is not about to be used. Optionally the load-relieving mechanism is configured such that the cam follower does not abut the edge of the cam track when the load-relieving mechanism is supporting the moving component and/or the part of the damping system. Again, this alleviates any stresses or wear that might otherwise occur, for example between the cam follower and the edge of the track.

In some arrangements it is desirable to monitor the number of doses dispensed from the multi-dose inhaler so that it can be determined how many doses remain. Therefore, in some arrangements the inhaler further comprises a counting mechanism for counting the number of times the canister drive moves from the rest position to the actuated position (or in alternative arrangements, from the actuated position to the rest position). The counting mechanism may be activated by any suitable configuration. For example the counting mechanism may comprise a pusher for driving the counting mechanism, the pusher engaged by a complementary feature of the canister drive, wherein movement of the canister drive from the rest position to the actuated position moves the complementary feature and pushes the pusher to count a completed actuation of the inhaler (or a completed reset of the inhaler in the alternative arrangement). This manner of driving the counter is thought to be particularly advantageous because the counter is directly driven by movement of the canister drive, and thus a reliable count should be achieved.

In accordance with the present invention, from a further broad aspect, there is provided a method of dispensing medicament from an inhaler, the inhaler comprising a drive mechanism comprising a canister drive for receiving a canister of medicament, a biasing means, and a trigger mechanism, the method comprising: holding the biasing means in a loaded configuration by a latch of the trigger mechanism wherein in a locked position the latch contacts the canister drive to prevent linear movement of the canister drive and holds the biasing means; and disengaging the latch from the canister drive in an unlocked position of the latch to release the biasing means from the loaded configuration to drive the canister drive from a rest position to an actuated position; wherein the trigger mechanism further comprises a blocker and the step of disengaging the latch from the canister drive comprises rotating the blocker in response to a force applied to the blocker from a blocking position in which it contacts the latch to block movement thereof from the locked position to the unlocked position to a rotated position in which the blocker is disengaged from the latch and allows movement of the latch from the locked position to the unlocked position.

Optionally the blocker comprises a flap, and the method comprises rotating the flap in response to a pressure drop within the inhaler and/or wherein the inhaler further comprises a button and the method comprises pushing the button to move the blocker from the blocking position to the rotated position.

Optionally the method further comprises deflecting a deflectable portion of an outer housing of the inhaler that is preferably formed by co-moulding a more deformable material with a more rigid material forming the remainder of the outer housing.

Optionally the method further comprises biasing the blocker into the blocking position with a blocker spring.

Optionally the method further comprises rotating the latch between the locked position and the unlocked position, and wherein the latch comprises a shelf configured for abutment with a ledge of the canister drive, the ledge protruding from the canister drive and biased to rest on the shelf under the load of the biasing means when the latch is in the locked position, wherein rotating the latch to the unlocked position tilts the shelf and the ledge disengages from the shelf to release the canister drive.

Optionally the method further comprises controlling the positioning of a canister received in the canister drive with at least one alignment guide. Optionally the at least one alignment guide comprises an integrally formed portion of the canister drive, preferably wherein one or more alignment guide(s) at least partially encircle a canister received in the canister drive, preferably having a close fit with the canister to guide or support the canister within the canister drive. Optionally the inhaler comprises a plurality of alignment guides, each guide at least partially encircling a portion of a canister received in the canister drive, the alignment guides substantially forming at least a partial circumferential ring around the canister.

Optionally the method further comprises counting the number of times the canister drive moves from the rest position to the actuated position (or from the actuated position to the rest position) by a counting mechanism that preferably comprises a pusher for driving the counting mechanism, the pusher engaged by a complementary feature of the canister drive, wherein movement of the canister drive from the rest position to the actuated position moves the complementary feature and pushes the pusher to count a completed actuation of the inhaler.

BRIEF DESCRIPTION OF THE DRAWINGS

Preferred aspects and embodiments of the present invention will now be described, by way of example only, with reference to the accompanying drawings, in which:

FIG. 4 is a side view of the prior art inhaler of FIGS. 1A and 1B,

FIG. 5 is a side view of an inhaler in accordance with embodiments of the present invention;

DETAILED DESCRIPTION OF PREFERRED EMBODIMENTS

Inhalers and methods of operating inhalers in accordance with embodiments of the present invention are illustrated in the figures.

Figure 1B:
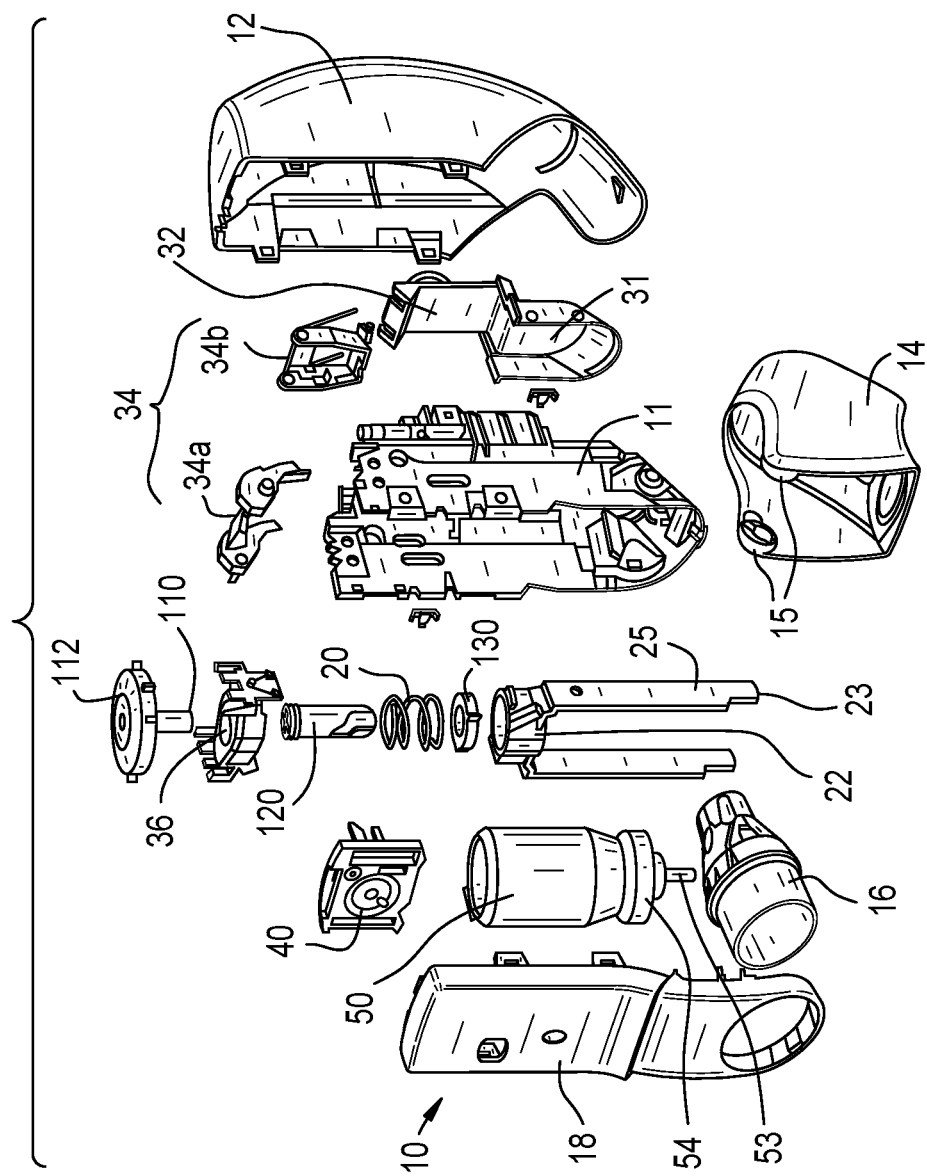
FIG. 1B is an exploded view of the prior art inhaler of FIG. 1A.
Figure 1A:
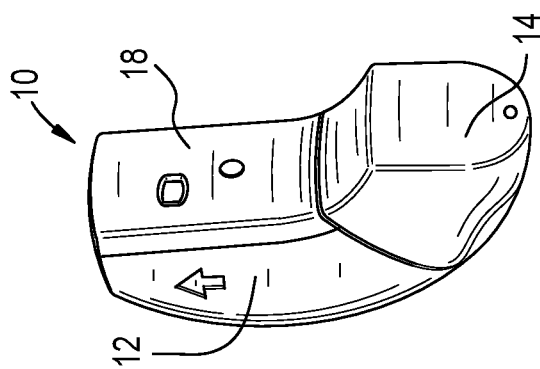
FIG. 1A is a perspective view of a prior art inhaler.
Figure 2:
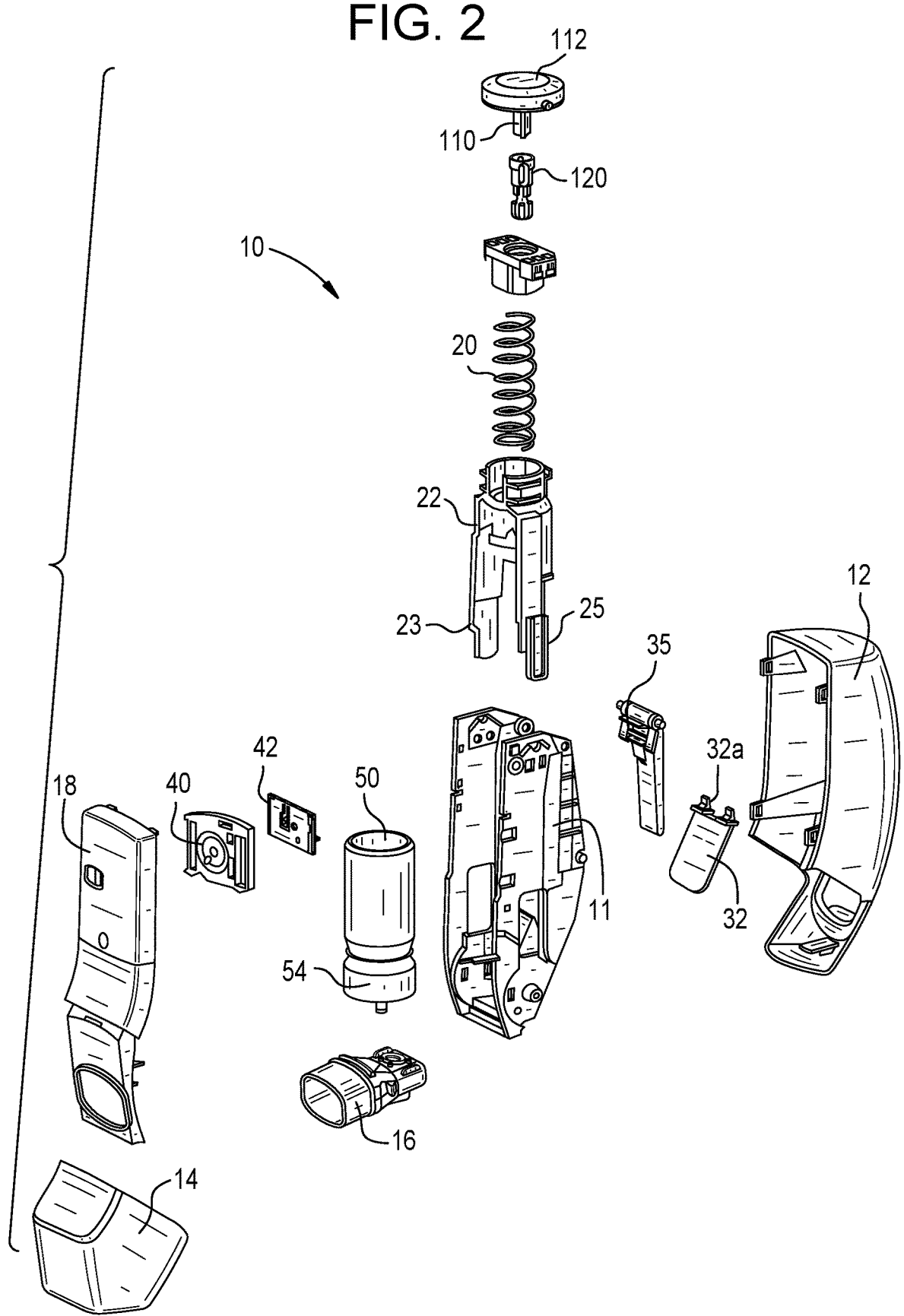
FIG. 2 is an exploded view of an inhaler in accordance with embodiments of the present invention.
Figure 3A:
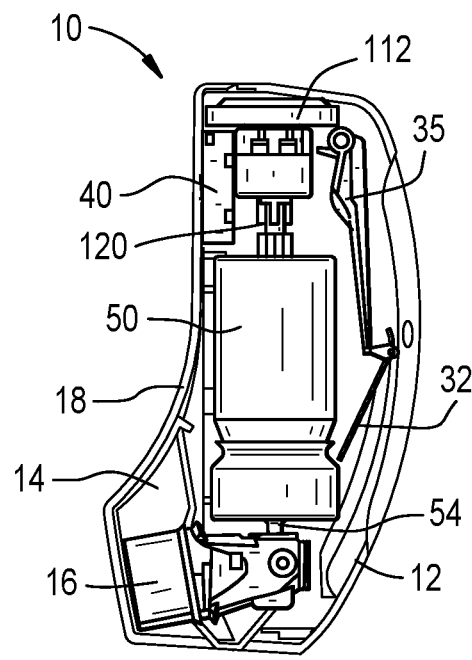
FIG. 3A is a side view of a portion of the inhaler of FIG. 2, highlighting the trigger mechanism in accordance with embodiments of the present invention.
Figure 3B:
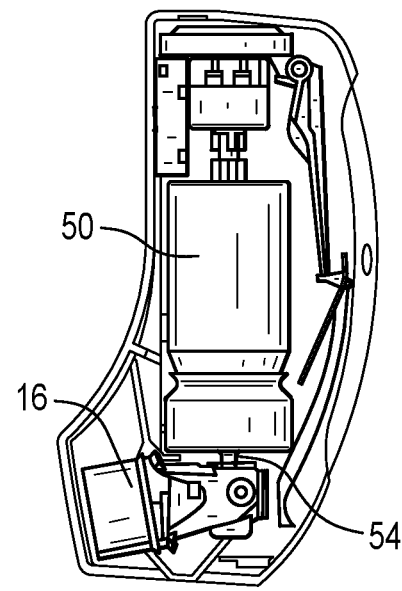
FIG. 3B is a side view of a portion of the inhaler of FIG. 2, highlighting the drug delivery components of the inhaler.
Figure 3C:
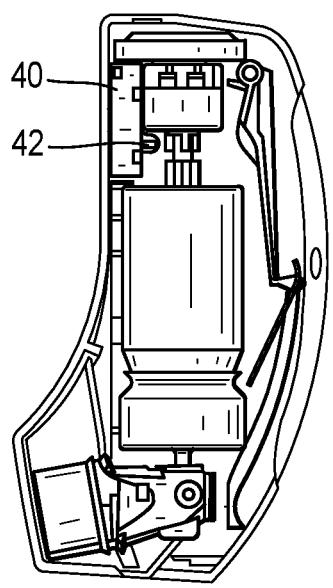
FIG. 3C is a side view of a portion of the inhaler of FIG. 2, highlighting the dose counting mechanism of the inhaler.
Figure 3D:
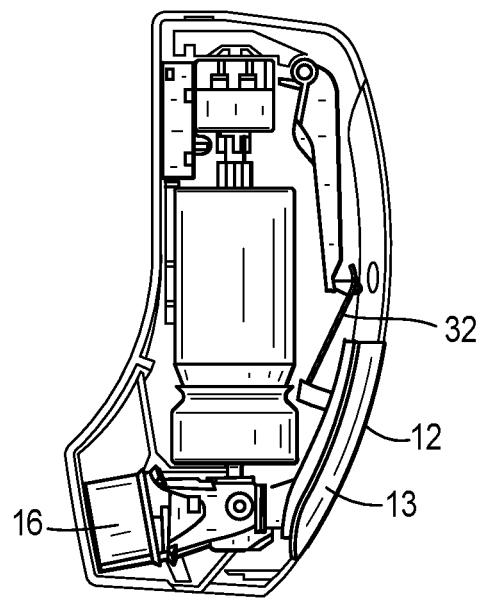
FIG. 3D is a side view of a portion of the inhaler of FIG. 2, highlighting the flow path through the inhaler.

Referring to FIGS. 1A and 1B, an inhaler 10 is shown, which in this illustration is a breath-triggered inhaler 10 with a breath-triggering mechanism 32, 34. The inhaler 10 of FIGS. 1A and 1B is similar to the prior art inhaler of WO 2013/038170, but with additional components compared with this earlier publication for damping return of the canister 50.

The inhaler 10 of FIGS. 1A and 1B has an outer housing or shell 12, which contains most of the components of the inhaler 10. At the base of the shell 12 there is a movable mouthpiece cover or cap 14 that pivots relative to the shell 12 to expose or cover the mouthpiece 16 of the inhaler 10. In combination with the front plate or fascia 18 of the inhaler 10, the shell 12 and cap 14 entirely enclose all the components of the inhaler 10 when in the closed configuration (as can be seen in FIG. 1A).

Inside the inhaler 10 there is a canister 50 that contains medicament. A valve 54 of the canister 50 has a metering chamber for metering a single dose of the medicament, as is known in the prior art. To dispense a dose of medicament, the canister 50 is compressed and a stem of the valve 54, which sits in a seat of the mouthpiece 16, is forced into the canister 50, which opens the valve 54 and the pressurised dose of medicament is expelled into the mouthpiece 16 for inhalation by the user. The canister 50 is compressed (indirectly through other components as discussed below) by a main spring 20 (shown in the exploded view of the inhaler 10 of FIG. 1B), which is held in a loaded position above the canister 50 and is released so as to expand downwardly in the inhaler 10. It is to be noted here that relative terms such as upwardly, downwardly, laterally, top, bottom, upper, lower, etc., are for ease of reference only and are not intended to be limiting in any way and are used in relation to the inhaler 10 being in its upright position for inhalation (as it is shown in most of the figures, both those of the prior art and of embodiments of the present invention).

The released spring 20 pushes downwardly on a yoke 22 of the inhaler 10. The yoke 22 is driven from its first, pre-fire position by the unloading spring 20 and moves rapidly to a second, fired position, which is determined by the lowermost portion of the yoke 22 coming into contact with another part of the inhaler 10. In the illustrated inhaler, the legs 25 of the yoke 22 have feet 23 that are driven into contact with bearing surfaces 15 of the opened cap 14 to halt the downward movement of the yoke 22.

Typically the spring 20 has a force in the range of, for example, about 35 to 60 N when compressed and therefore drives the yoke 22 rapidly to its fired position when released, for example in just a few milliseconds, such as around 4 ms. As the yoke 22 moves to its fired position, it interacts with a damping system of the inhaler 10, driving a rod 120 downwardly. The rod 120 forces the canister 50 downwards with sufficient force to drive the valve stem 53, which is held in the seat of the mouthpiece 16, into the canister 50 (so driving the canister from a rest position to an actuating position), thus opening the valve to allow the dose of medicament in the metering chamber of the valve 54 to be released into the mouthpiece 16.

The inhaler 10 comprises a mechanism for automating closure of the valve 54 by returning the canister 50 to its rest position soon after the current dose has been dispensed, irrespective of whether the user closes the cap 14 straight after using the inhaler 10. Furthermore, the automated closure of the valve 54 occurs within a predetermined time period and is sufficiently soon after dispensing the dose that it is unlikely, or even not possible, that the user will have reoriented the inhaler 10 from its upright position (i.e. the closure of the valve 54 occurs quickly enough that the user will not have reacted to any significant extent before the valve 54 is closed and so the valve 54 will close whilst the user still has the inhaler 10 in its upright, in use, position). As illustrated in FIG. 1B, the mechanism for automating resetting of the canister 50 and valve 54 comprises a damping system comprising a rotary damper 112 and a shaft 110 protruding therefrom. The rotary damper 112 controls (damps) rotational movement in at least one direction such that rotation of the shaft 110 is also controlled (damped) in at least one direction. Therefore forces acting on the shaft 110 will only rotate the shaft 110 at a speed determined by the damper 112. The shaft 110 of the damper 112 interacts with a rod 120. The rod 120 is generally elongate and has an inner bore along its central axis for receiving the shaft 110 of the rotary damper 112. The surface of the inner bore has a profile configured to provide a locking fit with the shaft such that the shaft 110 and the rod 120 are immovably fixed together in at least the direction of rotation about the rod 120 and shaft central axes. The surface of the inner bore of the rod 120 does not prevent axial movement of the rod 120 relative to the damper shaft 110. Therefore the rod 120 is able to slide in a linear, axial direction up and down the shaft. For ease of reference, movement in an upward direction (referring to FIG. 1, when the inhaler 10 is upright as shown) will be defined as in the distal direction and movement in a downward direction will be defined as in the proximal direction. So for the damping system 112 this is relative to the canister 50 (the damper 112 being distal from the canister 50 compared with the rod 120, for example) or in general distal and proximal are defined relative to the mouthpiece 16.

The damping system 112 is located in the inhaler 10 generally in the distal portion of the inhaler 10, above the canister 50. The damping system 112 is held in place by a cover 36 that is affixed to a chassis 11 that is configured to hold various parts of the inhaler 10 in position relative to the shell 12 or other parts of the inhaler 10. The rod 120 extends proximally from the damping system 112 and is received on the shaft of the rotary damper 110. The rod 120 passes through a yoke plate and teeth of the yoke plate protrude into tracks in the outer surface of the rod 120. The yoke plate is fixed within the yoke 22 at a distal end thereof, in a collar of the yoke 22. The yoke 22 is guided by the chassis 11 but is able to move relative to the chassis 11 in both the distal and proximal directions. A main spring 20 is located between the cover 36 and the collar of the yoke 22 and when released from a loaded configuration, the main spring 20 pushes downwardly on the yoke 22 and the yoke plate to move the yoke 22 and yoke plate in the proximal direction.

When the trigger mechanism releases the yoke 22, movement of the yoke 22 also causes the rod 120 to move and it is the rod 120 that pushes downwardly on the canister 50 to move the canister 50 to a fired position. Movement of the components from the rest position to the fired position is rapid and may occur in a very short time period, such as within a few milliseconds. Therefore the user receives a dose of medicament very quickly after they begin inhaling through the mouthpiece 16 of the inhaler 10. After the inhaler 10 has been fired the damper 112 is configured to release the downward force of the rod 120 on the base of the canister 50 in a controlled manner so as to reset the canister 50 (moving it from the actuated or fired position back to the rest position) and moving the canister valve stem 53 to its closed position. The canister valve 54 refills its metering chamber as the valve stem 53 closes. It is important that the movement of the canister valve stem 53 relative to the canister 50 (i.e. the firing of the valve 54 and its subsequent refilling and resetting) is controlled over a predetermined period of time that is neither too short nor too long, to avoid the firing and/or refilling being insufficient or incomplete.

In inhalers 10 known in the art, resetting of the inhaler 10 is achieved by closing the cap 14. The bearing surfaces 15 of the cap 14 are cams that impart an upward force on the feet 23 of the yoke 22 when the cap 14 is rotated by the user to its closed position to cover the mouthpiece 16. A latch mechanism 34 then engages to hold the spring 20 in its compressed state ready for the next actuation. Whilst the latch mechanism 34 of the prior art arrangement in FIG. 1B is effective, it comprises multiple components that are made of different materials and some require sub-assembly before assembling into the inhaler 10. It is possible that having so many components might introduce some reliability and robustness issues during assembly or during use. Furthermore, having multiple components of differing materials can be costly to manufacture and assemble.

Therefore the inhalers 10 according to embodiments of the present invention comprise an improved trigger mechanism for holding a canister drive 22 against movement under loading of a biasing means such as a spring 20 and for releasing the canister drive 22 to dispense a dose of medicament, and for being reset after dispensing ready to dispense a further dose. Unless otherwise specified, components described in relation to the prior art may be the same as the components according to embodiments of the present invention.

The trigger mechanism of embodiments of the present invention is illustrated in FIGS. 2, 3, 5, 6 and 8. Referring to FIG. 2, the trigger mechanism comprises a latch 35 and a blocker 32, which in FIG. 2 is a flap or vane that is rotatable when a force is applied to the flap 32. The force may be applied by a user inhaling through the mouthpiece 16 and thereby causing a pressure drop in the flow path (illustrated in FIG. 3D) and the flap 32 to pivot about its axis 32*a*. Alternatively or additionally, the force may be applied by activation of a button 30*b* (illustrated in FIGS. 7A and 7B) that flexes inwardly towards the flap 32 and the protrusion of the button 30*b* pushes the flap 32 so that it rotates to its rotated position, as discussed further below.

Referring to FIGS. 3A to 3D, the inhaler 10 is shown with various components highlighted in different figures for ease of explanation. FIG. 3A shows the trigger mechanism highlighted in red, comprising the latch 35 and the flap 32. In this figure, the inhaler 10 is closed and the feet 23 of the canister drive 22 (not shown) are supported by the bearing surfaces 15 of the closed cap 14. The load of the main spring 20 is thus supported by the bearing surfaces 15 through the legs 25 of the canister drive 22 and the canister drive 22 is designed to withstand such a load. Once the cap 14 is opened, the canister drive 22 moves downwardly and engages with the latch 35 as discussed in relation to FIGS. 6A to 6H below, FIG. 3B shows the components for dispensing a dose of medicament, particularly the canister 50 that contains the multiple doses of medicament, its valve stem 53 and the mouthpiece 16 through which a user inhales a dispensed dose.

FIG. 3C shows the location of the counter mechanism 40 and its pusher 42 that interacts with the canister drive 22 as discussed below in relation to FIGS. 11 to 14.

FIG. 3D shows the components of the inhaler 10 that define the flow path (and also the flap 32) and includes the outer housing or shell 12 and a co-moulded portion 13 thereof, which is discussed in more detail with reference to FIGS. 7 and 8.

Turning now to FIGS. 4 and 5, the difference between the trigger mechanisms of the prior art and the improved trigger mechanism of the inhalers 10 of embodiments of the present invention is illustrated. In FIG. 4, it can be seen that the prior art trigger mechanism requires six components for holding the canister drive or yoke 22 in its loaded configuration, for releasing the yoke 22 and for re-engaging the yoke 22 after a dispensed dose. The components of the prior art trigger mechanism include a lever 34*a* that engages the yoke 22 and rotates about a pivot in a chassis 11. The lever 34*a* of the prior art does not disengage from the yoke 22 at any stage, only rotates relative thereto. The lever 34*a* is locked against rotation by a lock member 34*b*, which also rotates between a position in which it stops rotation of the lever 34*a* and a position in which it allows the lever 34*a* to rotate on its pivot axis on the yoke 22. When at its rest position as shown in the figure, the lock 34*b* is biased into its position by a leaf spring 34*c*, which must be sonic welded to the lock 34*b* prior to assembly. The mechanism further comprises a vane 32, which again pivots between two positions to hold or release the lock 34*b*. However, to engage the vane 32 with the lock 34*b* there is further required an intermediate member which is a drop link 34*d* (and which may be an integral part of the lock 34*b*). Finally an additional component to define the flow path to the location at which the vane 32 is positioned is required, which is the duct cover 31, with integral push button 30*a*. In order for the button 30*a* to be accessible to the user, an aperture is provided through the outer shell 12 through which the button can be pressed.

In contrast, as shown in FIG. 5, embodiments of the present invention require only 2, or in some embodiments discussed below, only 3, components to form the trigger mechanism. There is provided a latch 35 that directly engages with the canister drive (or yoke) 22. Further detail of the engagement is discussed in relation to FIGS. 6A to 6H. The latch 35 is configured to disengage from the canister drive 22 in order to enable the canister drive 22 to move linearly (generally downwardly) under the load of the spring 20 (not shown). The second component of the trigger mechanism, the blocker or flap 32 engages with the latch 35 to block it from disengaging from the canister drive 22.

When the flap rotates about its pivot point 32a, the end of the latch 35 that abuts the flap 32 in the region of this pivot point is released to pass over the top of the flap 32, 32a and thus the top end of the latch 35 rotates away and disengages from the canister drive 22. Thus a simplified and reliable trigger mechanism is provided in accordance with embodiments of the present invention. Furthermore the position of the flap 32 of the embodiments of the present invention is closer to the mouthpiece 16 so the flow path is shorter than in prior art arrangements, providing an even more reliable triggering mechanism.

Referring to FIGS. 6A to 6H, the inhaler 10 according to embodiments of the present invention is shown in different operating states, from a ready to operate state, through to dispensing of a dose, resetting of the device and returning it to a rest and closed state as described below.

Figure 6A:
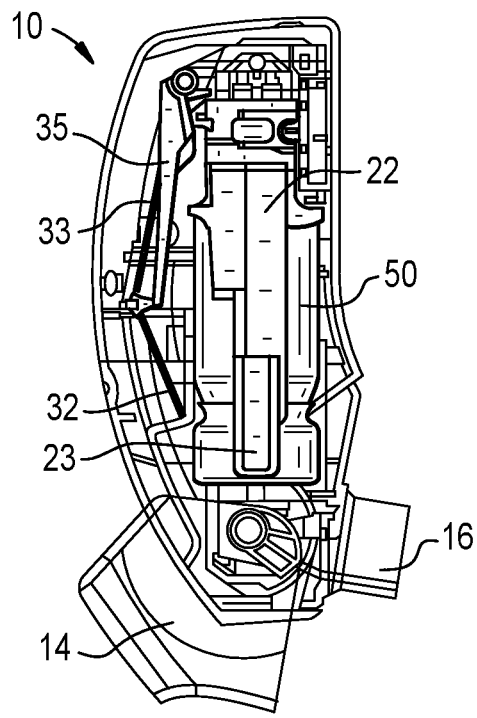
FIGS. 6A-6G are the other side view of the inhaler of FIG. 5 with additional inhaler components illustrated compared with FIG. 5 and showing the stages of operation of the trigger mechanism.

FIG. 6A shows the inhaler 10 in a ready-to-use configuration in which the cap 14 has been rotated to an open position to expose the mouthpiece 16. The cap 14 is not supporting the canister drive 22 when the cap 14 is open as the feet 23 of the canister drive 22 no longer rest on the bearing surfaces 15 of the cap 14. Therefore the load of the spring 20 biases the canister drive 22 downwardly, but the canister drive 22 is prevented from moving under the load of the spring 20 by the latch 35, which abuts a portion of the canister drive 22. The latch 35 is prevented from disengaging with the canister drive 22 by the flap 32, the top end of which 32a abuts the latch 35 and prevents it from rotating out of engagement with the canister drive 22. As can be seen in FIG. 6A, in this arrangement the trigger mechanism comprises a third component, a chassis spring 33 (as shown in FIG. 6D) that biases the flap 32 into its blocking position. The chassis spring 33 is an integrally formed elongate portion of a chassis of the inhaler 10 that is affixed (integrally formed) at a top end thereof and has a free and flexible lower tip that abuts a protrusion 32b at the top edge of the flap 32. Thus the inhaler 10 is locked in a ready-to-fire position by a simple and reliable trigger mechanism.

Figure 6B:
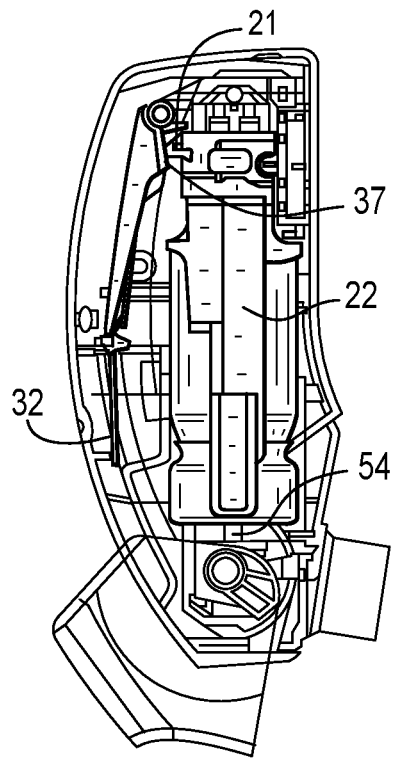
Figure 6C:
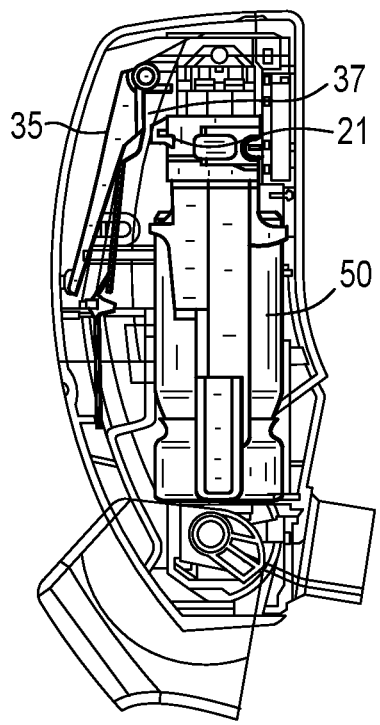
Figure 6D:
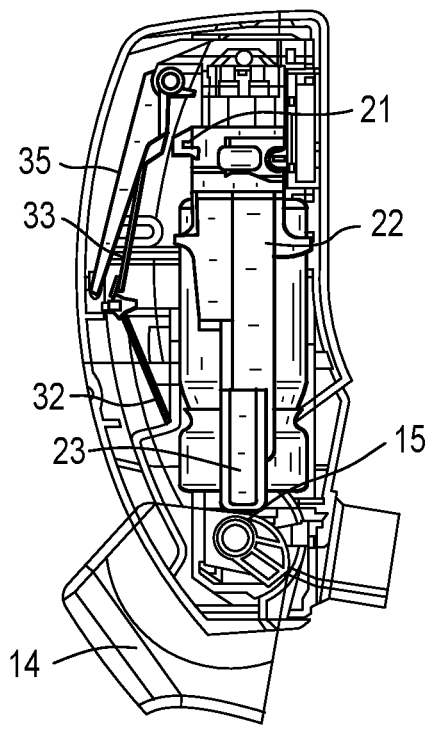
Figure 6E:
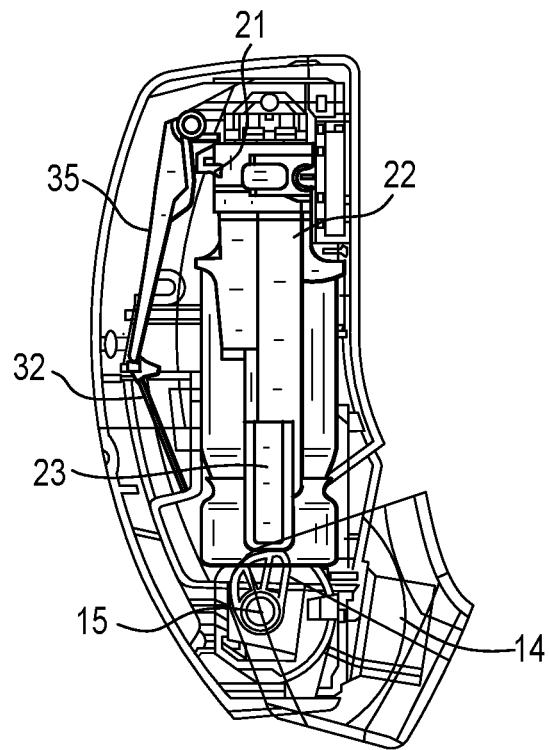

To dispense a dose of medicament from the canister 50, a user inhales through the mouthpiece 16 and causes a pressure drop in the flow path that rotates the flap 32 from its rest (blocking) position (shown in FIG. 6A) to a rotated (unblocking) position as shown in FIG. 6B. The chassis spring 33 is configured such that its biasing force is readily overcome by a typical inhalation of a user to allow the flap 32 to rotate. As the flap 32 rotates, its upper edge at the pivot point 32a rotates and the latch 35, which is biased (indirectly by the spring 20, not shown) to slide past and over the flap 32 when the flap 32 has rotated to a sufficient degree, passes over the flap 32 upper edge. Thus the latch 35 rotates about its pivot point and the upper portion of the latch 35 moves away from the canister drive 22. In FIG. 6B, the latch 35 is just passing over the top edge of the flap 32a and has not yet disengaged with the canister drive 22. This occurs in FIG. 6C, in which it can be seen that a shelf 37 of the latch 35 (best shown in FIG. 6H), that was underneath a ledge 21 of the canister drive 22 in FIG. 6B, has now moved just far enough away such that the ledge 21 disengages from the shelf 37 and the canister drive 22 is free to move downwardly under the load of the spring 20 (not shown). This also moves the canister 50 downwardly and compresses the valve stem 54 into the mouthpiece 16 and dispenses a dose into the mouthpiece 16. The user is still inhaling at this time so the dose is dispensed appropriately and with assistance from the user's inhalation.

Figure 6F:
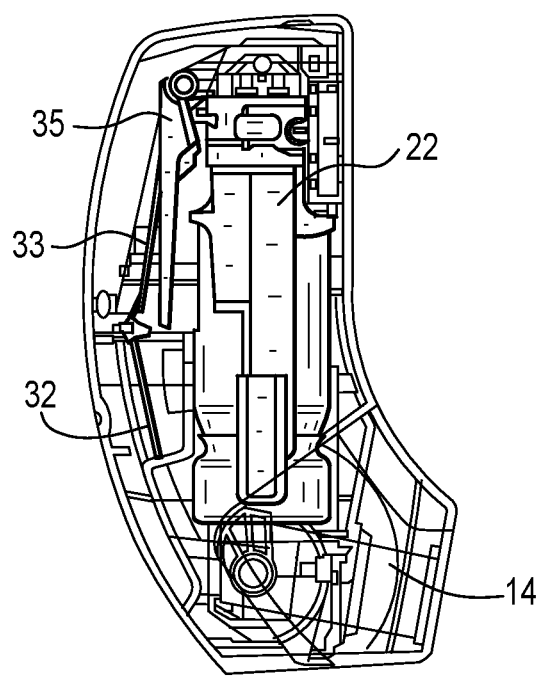
Figure 6G:
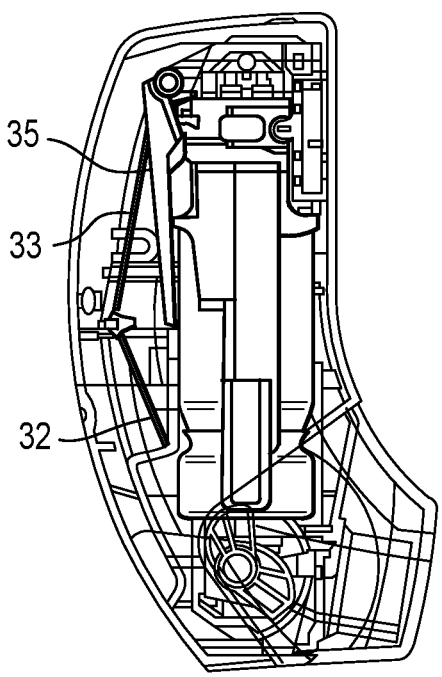
Figure 6H:
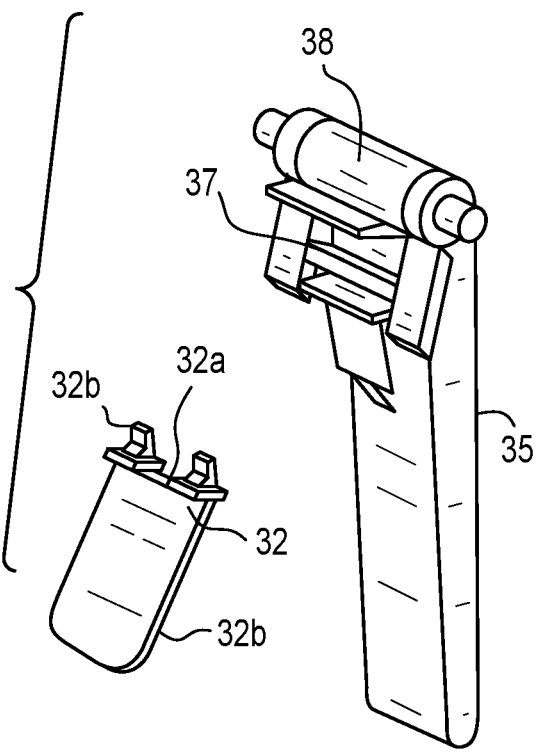
FIG. 6H shows enlarged views of the flap and of the latch of the trigger mechanism of FIGS. 6A-6G.

FIG. 6D shows the inhaler after a dose is dispensed and the user has stopped inhaling. The chassis spring 33 biases the flap 32 back to its initial position but the latch 35 remains in the unlocked position as there is no spring or other biasing means that returns the latch 35 at this stage. In order to reset the latch 35, the end of the latch 35 is pushed back over and past the top edge of the flap 32, which is now back in its blocking position. This is achieved by closing the cap 14, such that bearing surfaces 15 of the cap 14 rotate and push upwardly on the feet 23 of the canister drive 22, pushing the canister drive 22 back towards its loaded position and loading the spring 20 as the canister drive 22 moves upwardly. As shown in stages in FIGS. 6E and 6F, upward movement of the canister drive 22 pushes the latch 35 back into its locked position by engagement of the ledge 21 of the canister drive 22 with a resetting protrusion or ledge 38 of the latch 35 (best seen in FIG. 6H). As the ledge 21 pushes upwardly on the resetting ledge 38, the latch 35 rotates and is pushed back past the top of the flap 32. As shown in FIG. 6F, as it pushes past the flap 32, the flap 32 temporarily rotates back to the unblocking or rotated position as the force on the latch 35 pushes the flap 32 enough to overcome the biasing of the chassis spring 33. As soon as the latch 35 has passed the flap 32, the flap 32 rotates back to its blocking position under the force of the chassis spring 33. The latch 35 is returned to its locked position although the ledge 21 of the canister drive 22 is not resting on the shelf of the latch 35 as the load of the spring 20 in this closed position is being held by the abutment of the feet 23 of the canister drive 22 with the bearing surfaces 15 of the cap 14 until the cap 14 is rotated back into the open position to expose the mouthpiece 16 for a subsequent inhalation (as shown in FIG. 6A).

Figure 7A:
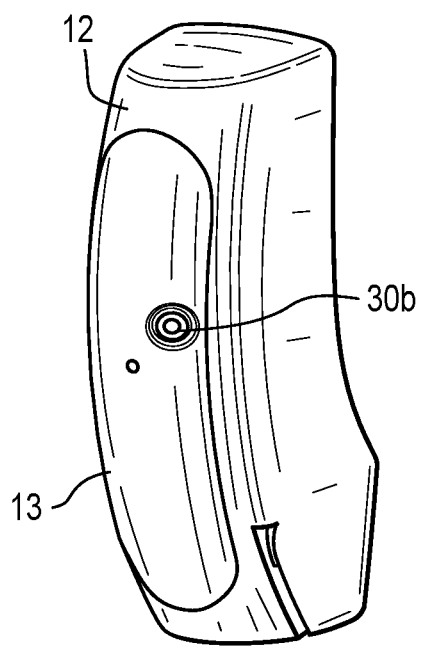
FIG. 7A is rear perspective view of an outer housing of an inhaler in accordance with embodiments of the present invention.
Figure 7B:
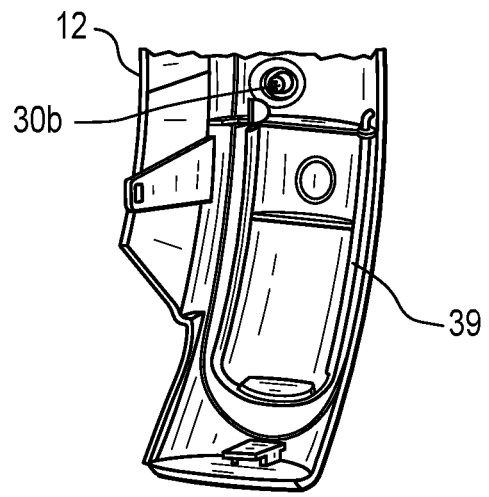
FIG. 7B illustrates the inside of the outer housing of FIG. 7A.
Figure 8:
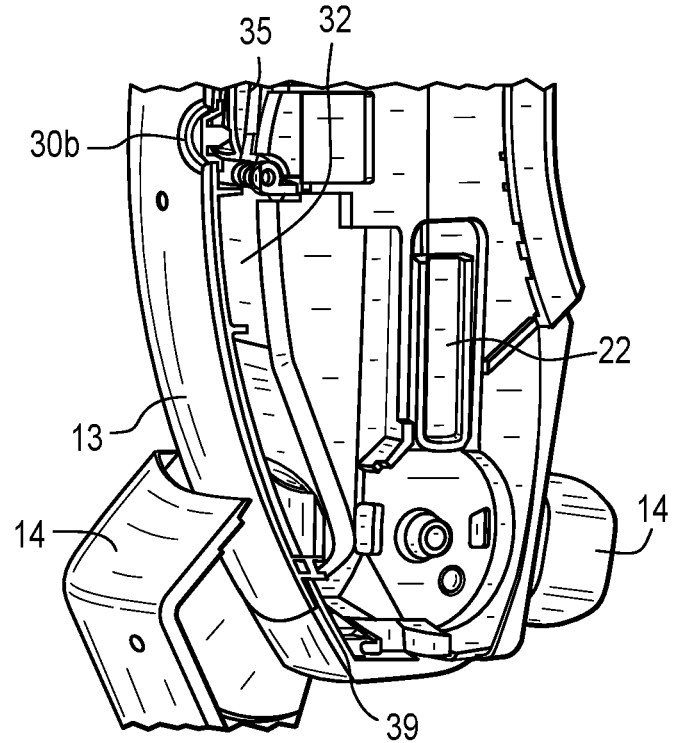
FIG. 8 illustrates components an inhaler in accordance with embodiments of the present invention, with a focus on the outer housing and trigger mechanism.

As discussed above, in some arrangements the inhaler 10 comprises a button 30b that is manually operable by a user, for example by being pushed with a finger, to activate the latch 35 and/or the flap 32 to trigger dispensing of a dose. The button arrangement as illustrated in FIGS. 7A, 7B and 8 is thought to be advantageous in its own right as it provides a manually activatable button 30b that does not have an aperture through which dirt or the like may ingress into the inhaler 10. As can be seen in FIG. 7A, the outer housing or shell 12 comprises a co-moulded portion 13 that has a button 30b integrally formed therewith. The co-moulded portion 13 is made from a flexible material, such as rubber or silicone or other suitable polymer that allows the button 30b to be pushed inwardly to press the latch 35 and/or the flap 32 to rotate the flap 32 to the rotated (unblocking) position. This arrangement is further advantageous because the co-moulded portion 13 protrudes from the inner surface of the outer shell 12, forming a soft seal 39 that helps to seal the flow path. This is most clearly seen in FIGS. 7B and 8.

Figure 9:
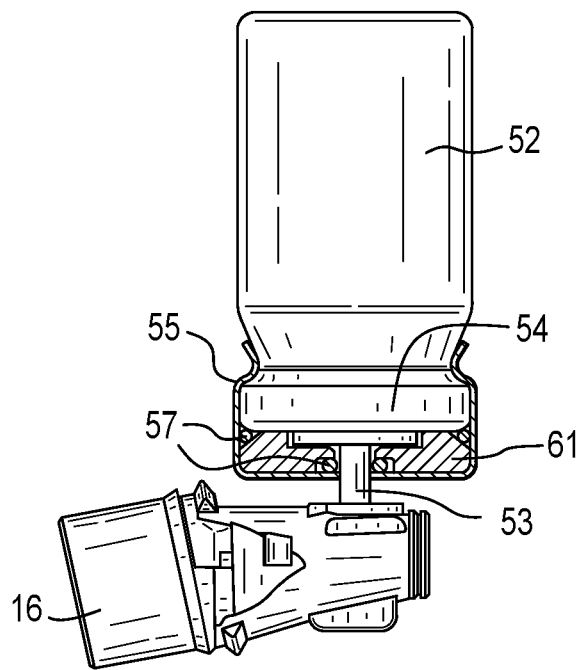
FIG. 9 illustrates a canister and mouthpiece arrangement for use with embodiments of the present invention.

As discussed above, the inhalers 10 of embodiments of the present invention comprise a canister drive 22 for receiving a canister 50 of medicament. FIG. 9 illustrates a canister 50 with a valve stem 53 inserted in a mouthpiece 16. The canister 50 is advantageously configured for use with inhalers 10 of the present invention and is provided with an aluminium collar 55 that crimps a desiccant puck 61 surrounding the valve stem 53, for improved performance over multiple doses. O-rings 57 seal the collar 55.

Figure 10A:
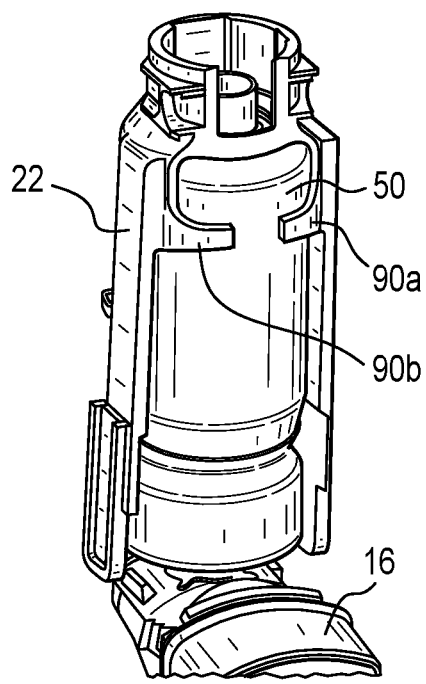
FIG. 10A illustrates a front view the canister drive in accordance with embodiments of the present invention having alignment guides for aligning the canister of FIG. 9.
Figure 10B:
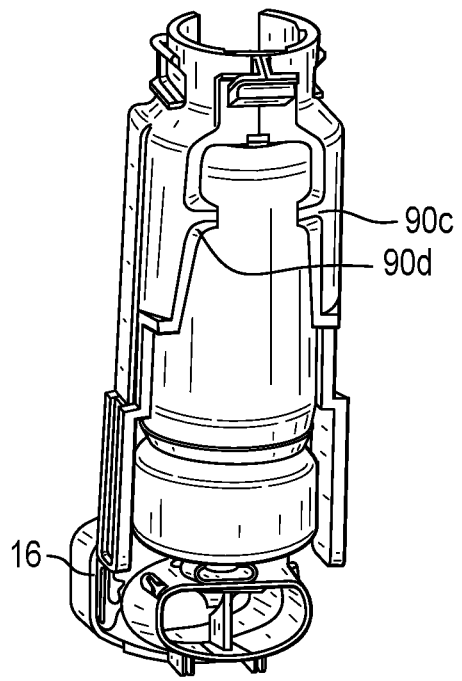
FIG. 10B illustrates the rear view of the canister drive of FIG. 10A, with further alignment guides.

During operation of the inhalers 10, particularly during driving of the canister 50 downwardly by the canister drive 22 to dispense a dose of medicament, it is desirable for the canister 50 to be aligned as precisely as possible relative to the mouthpiece 16 to avoid the valve stem 54 being compressed at any angle other than parallel to the axis of the canister 50. If the canister 50 tilts at all relative to the position in which the valve stem 54 is held in the mouthpiece 16, it is thought that this could detrimentally affect the compression of the canister 50 relative to the stem 54 and/or the time it takes for the valve to reset, potentially affecting the dosage. Therefore, as shown in FIGS. 10A and 10B, the inhalers 10 of some arrangements comprise at least one alignment guide 90a, 90b, 90c, 90d for controlling the positioning of a canister 50 received in the canister drive 22, such as when the canister 50 is driven by the canister drive 22 to the actuated position and/or when the canister 50 returns to the rest position. By guiding the canister 50 during motion, better alignment of the canister 50 is ensured and more reliable dosing and/or reset may be achieved.

As shown in FIGS. 10A and 10B, there is provided in some arrangements a plurality of alignment guides 90a, 90b, 90c, 90d integrally formed with the canister drive 22. This arrangement is thought to be particularly advantageous as the canister drive 22 drives the canister 50 as well as ensuring its alignment when driven. In the illustrated embodiment, the alignment guides 90a, 90b, 90c, 90d co-operate to partially encircle the canister 50 received in the canister drive 22. Thus the alignment guides 90a, 90b, 90c, 90d, substantially form a partial circumferential ring around the canister 50. In other arrangements, the alignment guides 90a, 90b, 90c, 90d substantially form a full circumferential ring around the canister 50. In the illustrated arrangement, the canister drive 22 comprises two opposed alignment guides 90a, 90b on a front side and two opposed alignment guides 90c, 90d on a back side, thus forming a partial circumferential ring with four segments. Other combinations of fewer or more alignment guides are envisaged. It is thought that such an arrangement is particularly advantageous because the canister 50 is held in alignment without significantly adding to the weight of the inhaler 10 as the alignment guides 90a, 90b, 90c, 90d are small and are arranged to support or guide the canister 50 as it moves in either direction.

Figure 11:
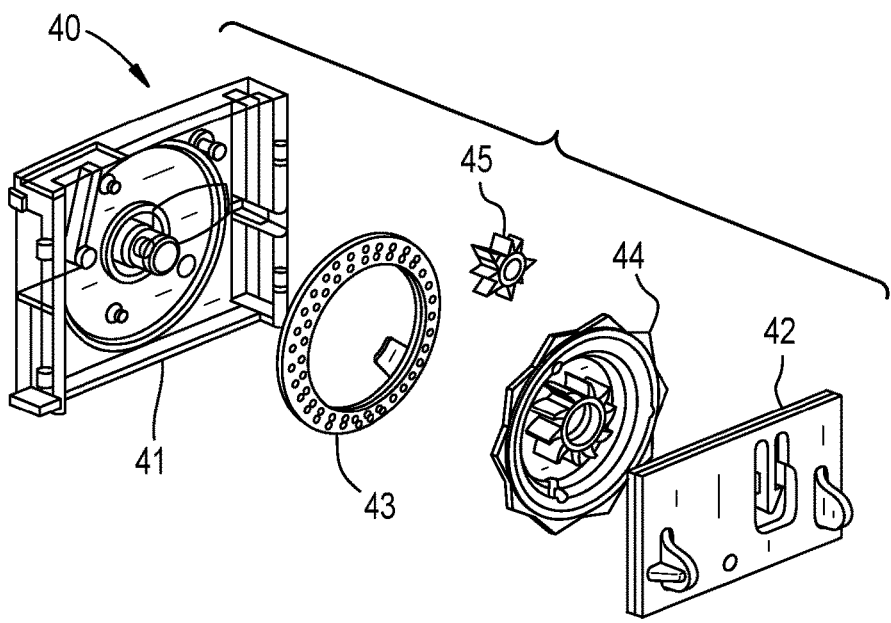
FIG. 11 illustrates the components of a counting mechanism in accordance with embodiments of the present invention.
Figure 12:
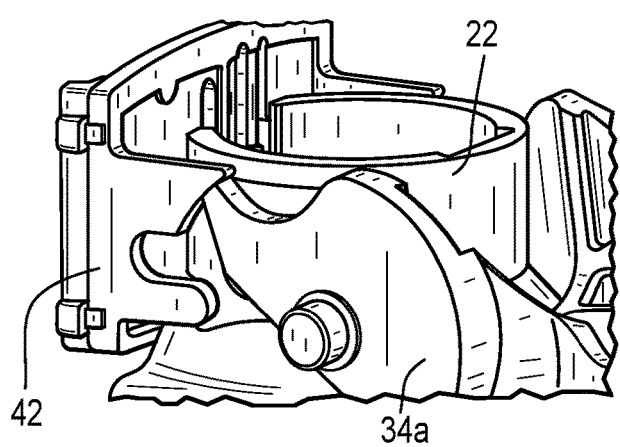
FIG. 12 is a section of a prior art counting mechanism interacting with a lever of the prior art inhaler.
Figure 13:
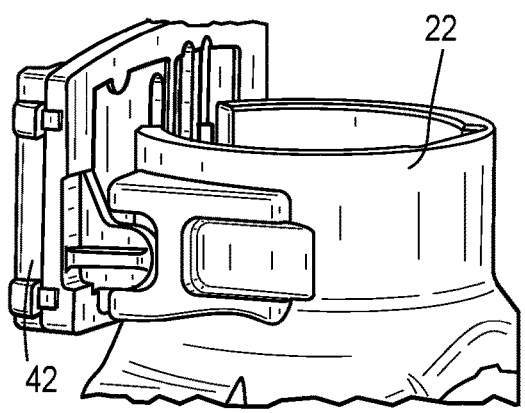
FIG. 13 illustrates the interaction of the counting mechanism of FIG. 11 with the canister drive of embodiments in accordance with the present invention.
Figure 14:
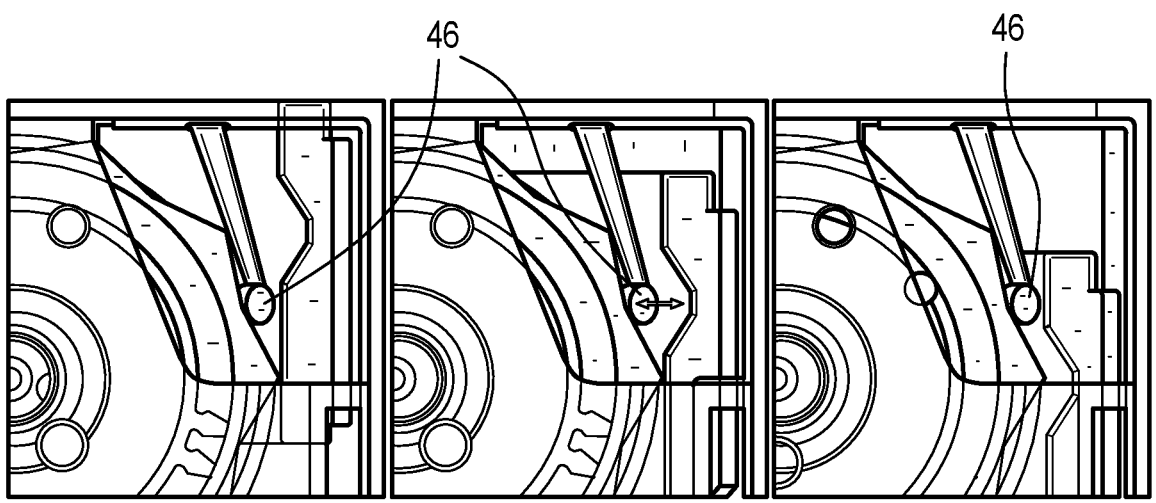
FIG. 14 illustrates a mechanism in accordance with embodiments of the present invention for controlling rotation of the count wheels of the counting mechanism of FIG. 11.

As is known in the art, it is desirable for many inhalers 10 to have a mechanism for determining how many doses have been dispensed from the inhaler 10 (and therefore how many may remain) and to provide such a dose count to the user. FIG. 11 illustrates a counting mechanism 40 in accordance with embodiments of the present invention. Similar to the prior art mechanisms, the counter 40 comprises a counter chassis 41, a tens wheel 43 and a units wheel 44 with an intermediate wheel 45 between them, and a pusher 42 for rotating the wheel(s) as appropriate. However the counter pusher 42 of FIG. 11 is driven directly by the canister drive 22, as shown in FIG. 13, whereas prior art counters are driven indirectly, for example by a lever 34a that pivots on the canister drive yoke 22 as shown in FIG. 12. This simplifies the counter 40 compared with the prior art and may improve reliability and robustness and may reduce the size of the counter 40 and thus of the inhaler 10 overall. A further improvement over the counters 40 of the prior art is the provision of a single component, a spring arm 46, for controlling both forward and backward rotation of the wheel(s), particularly the unit wheel 44, as illustrated in FIG. 14. This enables a more compact and slimmer counter 40 to be provided.

Therefore inhalers in accordance with the embodiments of the present invention address at least one of the drawbacks of the prior art, providing a compact and robust triggering mechanism and/or canister guiding means to improve performance of the inhaler and its reliability and consistency between doses over the full lifetime of the device.

The invention claimed is:

1. An inhaler (10) for delivery of a medicament by inhalation, the inhaler (10) comprising:

a drive mechanism comprising a canister drive (22) for receiving a canister (50) of medicament, a biasing means (20), and a trigger mechanism;

the trigger mechanism comprising:

a latch (35) having:

a locked position in which the latch contacts the canister drive (22) to prevent linear movement of the canister drive (22) and holds the biasing means (20) in a loaded configuration; and an unlocked position in which the latch (35) is disengaged from the canister drive (22) and releases the biasing means (20) from the loaded configuration to drive the canister drive (22) from a rest position to an actuated position; and a blocker (32) having:

a blocking position in which the blocker contacts the latch (35) to block movement thereof from the locked position to the unlocked position; and a rotated position in which the blocker is disengaged from the latch (35) and allows movement of the latch (35) from the locked position to the unlocked position; and the blocker (32) is rotatable in response to a force applied to the blocker (32); and wherein the inhaler further comprises a blocker spring (33) for biasing the blocker (32) into the blocking position, and wherein the blocker spring (33) is configured to abut a protrusion of the blocker (32).

2. The inhaler of claim 1, wherein the blocker (32) comprises a flap, and the flap is rotatable in response to a pressure drop within the inhaler and/or wherein the inhaler further comprises a button (30b) for moving the blocker (32) from the blocking position to the rotated position.

3. The inhaler of claim 2, further comprising an outer housing (12) for encasing the drive mechanism, wherein the button (30b) comprises a deflectable portion of the outer housing (12), formed by co-moulding a more deformable material with a more rigid material forming the outer housing.

4. The inhaler of claim 1, further comprising a chassis (11) for at least partially receiving at least one or more of the canister drive (22), the biasing means (20), the latch (35) and the blocker (32).

5. The inhaler of claim 2, wherein the latch (35) is rotatable between the locked position and the unlocked position and further comprises a shelf (37) configured for abutment with a ledge (21) of the canister drive (22), the ledge (21) protruding from the canister drive (22) and biased to rest on the shelf (37) under the load of the biasing means when the latch (35) is in the locked position and further wherein rotation of the latch (35) to the unlocked position tilts the shelf (37) and the ledge (21) disengages from the shelf (37) to release the canister drive (22).

6. The inhaler of claim 1, further comprising at least one alignment guide (90) for controlling the positioning of the canister (50) received in the canister drive (22).

7. The inhaler of claim 6, wherein the at least one alignment guide (90) comprises an integrally formed portion of the canister drive (22).

8. The inhaler of claim 6, wherein the at least one alignment guide (90) at least partially encircle the canister (50) received in the canister drive (22), having a close fit with the canister (50) to guide or support the canister (50) within the canister drive (22).

9. The inhaler of claim 1, further comprising a resetting mechanism for resetting the drive mechanism, the resetting mechanism configured for moving the canister drive (22)

back to the rest position to reload the biasing means (20) and to reset the trigger mechanism to the locked position.

10. The inhaler of claim 9, wherein the resetting mechanism comprises a rotatable cover (36) configured to drive the canister drive (22) back to the rest position under rotation of the cover (36), wherein movement of the canister drive (22) towards the rest position brings a ledge (21) of the canister drive (22) into engagement with a resetting protrusion on the latch (35) to move the latch back into the locked position.

11. The inhaler of claim 1, further comprising a return mechanism for returning the canister (50) received in the canister drive (22) from a fired position to a ready-to-fire position, the return mechanism comprising a damping system (112), the damping system (112) configured to enable the canister to automatically return from the fired position to the ready-to-fire position within a predetermined time period measured from the release of the biasing means (20) from the loaded configuration.

12. The inhaler of claim 1, further comprising a counting mechanism (40) for counting the number of times the canister drive (22) moves from the actuated position to the rest position.

13. The inhaler of claim 12, wherein the counting mechanism comprises a pusher (42) for driving the counting mechanism, the pusher (42) engaged by a complementary feature of the canister drive (22), wherein movement of the canister drive (22) from the rest position to the actuated position moves the complementary feature and pushes the pusher (42) to count a completed actuation of the inhaler.

\* \* \* \* \*